United States Patent
Ephraim et al.

(10) Patent No.: US 11,337,958 B2
(45) Date of Patent: May 24, 2022

(54) COMPOSITIONS AND METHODS OF TREATING AND REDUCING RISK OF CONDITIONS ASSOCIATED WITH ELEVATED 4-ETHYLPHENYL SULFATE

(71) Applicant: Hill's Pet Nutrition, Inc., Topeka, KS (US)

(72) Inventors: Eden Ephraim, Lawrence, KS (US); Dennis Jewell, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 83 days.

(21) Appl. No.: 16/721,413

(22) Filed: Dec. 19, 2019

(65) Prior Publication Data

US 2021/0186928 A1    Jun. 24, 2021

(51) Int. Cl.
| | |
|---|---|
| *A61K 31/375* | (2006.01) |
| *A61P 25/22* | (2006.01) |
| *A61K 9/00* | (2006.01) |
| *A61K 36/48* | (2006.01) |

(52) U.S. Cl.
CPC .......... *A61K 31/375* (2013.01); *A61K 9/0056* (2013.01); *A61K 36/48* (2013.01); *A61P 25/22* (2018.01)

(58) Field of Classification Search
None
See application file for complete search history.

(56) References Cited

U.S. PATENT DOCUMENTS

| | | | | |
|---|---|---|---|---|
| 6,255,341 B1 * | 7/2001 | DeMichele | ............ | A61P 39/06 514/474 |
| 7,258,879 B1 * | 8/2007 | Hodge | ................ | A23K 20/158 426/2 |
| 2009/0018072 A1 * | 1/2009 | Scheele | ................... | A23L 33/17 514/7.4 |
| 2010/0233320 A1 * | 9/2010 | Sunvold | ................ | A23K 10/18 426/62 |

FOREIGN PATENT DOCUMENTS

| | | | |
|---|---|---|---|
| CN | 102228255 | * | 11/2011 |
| CN | 103125777 | A | 6/2013 |
| CN | 104431597 | A | 3/2015 |
| CN | 103444987 | B | 4/2015 |
| JP | 2007/091656 | * | 4/2007 |
| JP | 2007-091656 | A | 4/2007 |
| WO | 01/17364 | A1 | 3/2001 |
| WO | 01/45517 | A1 | 6/2001 |
| WO | 2013/095412 | A1 | 6/2013 |
| WO | 2018/215759 | A1 | 11/2018 |

OTHER PUBLICATIONS

International Search Report and the Written Opinion of the International Searching Authority issued in International Application PCT/US2019/067564 dated Sep. 14, 2020.

* cited by examiner

*Primary Examiner* — Ralph J Gitomer

(57) ABSTRACT

Compositions and methods are disclosed for treating anxiety or stress in an animal, for reducing elevated levels of 4-EPS in an animal with elevated 4-EPS levels, for preventing elevated levels of 4-EPS in an animal and for promoting growth of beneficial microbes in an animal's microbiome and inhibiting growth of non-beneficial microbes. The methods comprise administering to the animal an effective amount of soy protein and vitamin C. Compositions are disclosed which comprise amounts of soy protein and vitamin C effective for use in the methods.

18 Claims, No Drawings

COMPOSITIONS AND METHODS OF TREATING AND REDUCING RISK OF CONDITIONS ASSOCIATED WITH ELEVATED 4-ETHYLPHENYL SULFATE

BACKGROUND

The microbial toxin, 4-ethylphenyl sulfate (4-EPS) is a metabolite produced by gut bacteria. Among other microbial metabolites, 4-EPS enters the systemic circulation. Increased levels of 4-EPS in the blood is associated with stress, anxiety, brain damage and other behavioral issues. Reduction in levels of 4-EPS has been shown to alleviate symptoms of stress and anxiety.

Canine anxiety (anxiety) is a response to fear and agitation, or apprehension when the dog anticipates a threat or fearful situation. Some individual dogs experience disproportionate levels of anxiety. Anxiety can develop into an anxiety disorder and can lead to behavioral and other issues. Some dogs experience a generalized anxiety, in which the fearful reaction is displayed in a wide range of situations to which a "normal" pet would be unlikely to react. Anxiety can take the form of one of various anxiety disorders such as generalized anxiety disorders, excessive stimulus anxiety, separation anxiety, confinement, noise phobias, among others.

Causative factors may include genetic components, prenatal and neonatal stressors, maternal separation, lack of socialization, unfamiliarity, or a previous unpleasant outcome during encounters with the stimulus (or similar stimuli). The most common causes are fear, separation and aging. Fear-related anxiety can be caused by loud noises, strange people or animals, visual stimuli, new or strange environments, and specific situations among others. Age-related anxiety affects older dogs and can be associated with cognitive dysfunction syndrome (CDS). Separation anxiety is a specific anxiety arising from an inability of the pet to find comfort when separated from family members. About 14% of dogs have separation anxiety. Some separation anxiety may be the result of dysfunctional attachment as a puppy ages and matures. In some cases, separation anxiety may arise in cases involving a change in household or daily routine, while in others separation anxiety is associated with an underlying state of anxiety along with other behavioral issues such as phobias.

Anxiety may lead to destructive behavior (particularly at exits or toward owner possessions), distress vocalization, house-soiling, salivation, pacing, restlessness, inability to settle, anorexia, and repetitive or compulsive behaviors. In some instances, anxiety may play a role in aggressive behavior.

Common symptoms of dog anxiety include aggression, urinating or defecating in the house, drooling, panting, destructive behavior, depression, excessive barking, pacing, restlessness and repetitive or compulsive behaviors. Different dogs display different symptoms and combinations of symptoms when suffering from anxiety.

Canine stress is the response of dog to a demand placed upon it to change or adapt, typically exhibited as feelings of strain or pressure. Dogs experiencing stress may result in feelings of fear, agitation, hyperactivity, nervousness, oversensitivity or irritability. Negative stress, excessive stress and chronic stress can have a detrimental effect on behavior, health and overall well-being. Stress has the potential to bring on illness, suppress the immune system, cause undesirable behaviors, and increase arousal, which increases the probability of aggressive behavior.

Causes of stress in dogs include grief, exposure to conflict, excessive or insufficient stimulation, overcrowded conditions, environmental changes (schedule, people, animals, increased noise); punitive training, insufficient social time, frightening events, neglect, frustration, and uncertainty among others.

Dogs communicate that they are experiencing stress in different ways. Some indications that a dog is experiencing stress include dilated pupils, tightness around eyes, whale eye/half-moon eyes, yawning, lip/nose licking, panting, excess salivation, smiling, teeth chattering, cheek puffing, showing teeth, wrinkled muzzle, pinned back or upright ears. Other indications include tense body, stretching, excessive shedding, little or no movement, low body posture, weight shifted back, trembling/shaking, penis crowning, sweaty paws, tight brow, barking, growling, howling and whining. When stressed, a dog's behavior will often change. Common behaviors that are often stress induced include restlessness, insufficient or excessive sleeping, jumpiness/hypervigilance, irritability, excessive self-grooming, destructive behavior, loss of appetite, obsessive/compulsive behaviors, inability to focus, hyperactivity, increased urination and defecation, and vomiting and diarrhea among others.

There is a need for methods and compositions for reducing elevated levels of 4-EPS, particularly in canines. There is a need for methods and compositions for treating or reducing the severity of elevated levels of canine anxiety. There is a need for methods and compositions for treating or reducing the severity of elevated levels of canine stress.

BRIEF SUMMARY

Methods for treating anxiety or stress in an animal are provided. The methods comprise administering to the animal effective amounts of soy protein and vitamin C.

Methods for reducing elevated levels of 4-EPS in an animal with elevated 4-EPS levels are provided. The methods comprise administering to the animal effective amounts of soy protein and vitamin C.

Methods for preventing elevated levels of 4-EPS in an animal are provided. The methods comprise administering to the animal at risk of elevated 4-EPS levels effective amounts of soy protein and vitamin C.

Methods for promoting growth of beneficial microbes in an animal's microbiome and inhibiting growth of non-beneficial microbes are provided. The methods comprise administering to the animal effective amounts of soy protein and vitamin C.

Compositions for treating anxiety or stress in an animal are provided. The compositions comprise effective amounts of soy protein and vitamin C.

Compositions for reducing elevated levels of 4-EPS in an animal with elevated 4-EPS levels are provided. The compositions comprise effective amounts of soy protein and vitamin C.

Compositions for preventing elevated levels of 4-EPS in an animal are provided. The compositions comprise effective amounts of soy protein and vitamin C.

Compositions for promoting growth of beneficial microbes in an animal's microbiome and inhibiting growth of non-beneficial microbes are provided. The compositions comprise effective amounts of soy protein and vitamin C.

DETAILED DESCRIPTION

The following description of the preferred embodiment(s) is merely exemplary in nature and is in no way intended to limit the invention, its application, or uses.

As used herein and in the appended claims, the singular forms "a", "an", and "the" include plural reference unless the context clearly dictates otherwise.

As used herein, the term "companion animal" includes any non-human animal suitable for being kept as a pet by humans including without limitation, a dog, a cat, rabbit and a rodent. Specific embodiments are formulations and methods of treatment for dogs and/or cats. In one specific aspect, the present invention is directed to formulations and methods of treatment for dogs.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

Methods are provided for treating anxiety and stress in an animal, particularly a companion animal such as a canine or feline. The methods comprise administering to the animal a combination of effective amount of both soy protein and vitamin C. The compositions comprise soy protein and vitamin C in effective amounts. The effective amount of soy protein is 3.7-6.9% of daily nutritional intake, and in some embodiments 4.8-5.8% of daily nutritional intake, and in some embodiments 5.3% of daily nutritional intake. The effective amount of vitamin C is 104.8-148.2 ppm of daily nutritional intake, and in some embodiments 119.1-137.9 ppm of daily nutritional intake, and in some embodiments 126.5 ppm of daily nutritional intake.

"Daily nutritional intake" and "total nutritional intake per day" refers to dry matter intake per day. That is, water weight is not included in calculating the amount of nutrition consumed per day. To the extent that food and food ingredient contain water/moisture, the dry matter represents everything in the sample other than water including protein, fiber, fat, minerals, etc. Dry matter weight is the total weight minus the weight of any water. Dry matter intake per day is calculated as the total nutritional intake per day excluding all water. For example, an amount of an ingredient equal to a specific percent of daily nutritional intake refers to the amount of that ingredient in dry matter form (i.e. excluding all water) relative to the total amount of dry matter consumed (also excluding all water) in a day. The skilled artisan would readily recognize and understand nutritional amounts and percentages expressed as dry matter amounts, dry matter weights and dry matter percentages. Since foods, whether wet, moist or dry, generally contain as certain amount of water, when calculating daily dry matter intake, the water component of such food is excluded. To calculate total daily nutritional intake, which is dry matter intake per day, water is excluded. To calculate percent of an ingredient of total daily intake on a dry matter basis, water is removed from the total intake to give total daily dry matter intake and the percent of the ingredient is based on amount of ingredient present as dry matter.

The compositions useful in the methods may be a pet food composition such as a dog food composition. Alternatively, soy protein and vitamin C may be administered as a supplement, a treat or toy or otherwise not incorporated into the food provided to the animal for daily nutritional intake.

In some preferred embodiments, the animal is a canine and the methods comprise administering to the canine effective amounts of soy protein and vitamin C daily. The effective amount of soy protein administered to the canine per day is 3.7-6.9%, of daily nutritional intake, and in some embodiments 4.8-5.8%, of daily nutritional intake, and in some embodiments 5.3% of daily nutritional intake. The effective amount of vitamin C administered to the canine per day is 104.8-148.2 ppm of daily nutritional intake, and in some embodiments 119.1-137.9 ppm vitamin C of daily nutritional intake, and in some embodiments 126.5 ppm vitamin C of daily nutritional intake. The compositions preferably are dog food compositions that comprise the daily effective amounts of soy protein and vitamin C.

Compositions and methods for the treatment of anxiety or stress in an animal, particularly in companion animals such as felines and canines, are provided. The compositions and methods are useful to treat a symptom of anxiety or stress in such animals that are in need thereof. The compositions and methods are useful to treat a symptom of anxiety or stress in such animals that have elevated levels of 4-EPS. The compositions and methods are useful to reduce elevated levels of 4-EPS in an animal that has elevated levels of 4-EPS, such as companion animals, particularly canines. In some embodiments, the compositions and methods for the treatment of canine anxiety or canine stress in a canine.

As used herein, the term "treatment" refers to eliminating, reducing the severity or preventing one or more symptoms.

As used herein, the term "anxiety" refers to anxiety, anxiety disorders and symptoms of anxiety and anxiety disorders.

As used herein, the term "stress" refers to stress, stress disorders, and symptoms of stress and stress disorders.

As used herein, the terms "treatment" with reference to anxiety refers to therapeutic and/or prophylactic activity. In a canine with symptoms of anxiety, treatment of canine anxiety refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine anxiety, a canine may be identified as having symptoms of anxiety. In some embodiments, a canine may be treated for anxiety without identifying symptoms of anxiety prior to treatment. In some embodiments, prior to treatment for anxiety, a canine may be identified as being predisposed to having or developing anxiety. In some embodiments, prior to treatment for anxiety, a canine may be identified as having elevated levels of 4-EPS.

As used herein, the terms "treatment" with reference to stress and stress disorders refers to therapeutic and/or prophylactic activity. In a canine with symptoms of stress or a stress disorder, treatment of canine stress refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine stress, a canine may be identified as having symptoms of stress or a stress disorder. In some embodiments, a canine may be treated for stress or a stress disorder without identifying symptoms of anxiety prior to treatment. In some embodiments, prior to treatment for stress or a stress disorder, a canine may be identified as being predisposed to having or developing stress or a stress disorder. In some embodiments, prior to treatment for stress or a stress disorder, a canine may be identified as having elevated levels of 4-EPS.

As used herein, the terms "treatment" with reference to promoting beneficial microbial growth and inhibition of harmful microbial growth refers to therapeutic and/or prophylactic activity. In a canine with reduced levels of beneficial microbes and elevated levels of harmful microbes, treatment for arresting levels of beneficial microbes and harmful microbes or promoting beneficial microbial growth and inhibiting harmful microbial growth. A canine identified as being predisposed to inhibiting beneficial microbial growth and promoting harmful microbial growth prior to initiating treatment. Treatment that initially promotes beneficial microbial growth and inhibits harmful microbial growth in an animal with elevated levels of harmful microbes and reduced levels of beneficial microbes, increases levels of beneficial microbes and decreases levels of harmful microbes to a more healthful balance and thereafter the continuing treatment maintains levels. In some embodiments, prior to treating for canine stress, a canine may be identified as having elevated levels of harmful microbes and reduced levels of beneficial microbes. In some embodiments, a canine may be treated without identifying elevated levels of harmful microbes and reduced levels of beneficial microbes in the animal.

As used herein the terms "treatment of elevated 4-EPS", "treating for elevated 4-EPS" and "treating elevated 4-EPS" refer to therapeutic and/or prophylactic activity in which 4-EPS levels are reduced. In a canine with elevated 4-EPS levels, "treatment of elevated 4-EPS", "treating for elevated 4-EPS" and "treating elevated 4-EPS" refers to reducing elevated 4-EPS levels. Treatment may lower elevated 4-EPS levels to normal, non-elevated levels or to reduced elevated 4-EPS levels. Following reduction of elevated 4-EPS levels, treatment may prevent elevation of 4-EPS levels or reduce severity of further development of elevated 4-EPS levels. In a canine that does not have elevated 4-EPS levels, "treatment of elevated 4-EPS", "treating for elevated 4-EPS" and "treating elevated 4-EPS" refers to arresting or lowering of 4-EPS levels, and preventing development of elevated 4-EPS levels or reducing severity of development of elevated 4-EPS levels. In some embodiments, prior to treating for 4-EPS, a canine may be identified as having elevated 4-EPS by measuring 4-EPS levels. In some embodiments, a canine may be treated for elevated 4-EPS without measuring 4-EPS levels prior to treatment. In some embodiments, prior to treating for 4-EPS, a canine may be identified as being predisposed to elevated 4-EPS. A canine identified as being predisposed to elevated 4-EPS may at the time of treatment have elevated 4-EPS, in which case the treatment is therapeutic, or may not have elevated 4-EPS, in which case the treatment is prophylactic, or treatment may be undertaken without determining 4-EPS levels. In some embodiments, a canine may be identified as being predisposed to elevated 4-EPS prior to initiating treatment with or without measuring 4-EPS levels.

As used herein, "an amount effective," "an effective amount," "effective amounts," and like terms refer to that amount of a soy protein and vitamin C effective to achieve a particular biological result, i.e., treatment of elevated levels of 4-EPS, anxiety, stress, and levels of beneficial and harmful microbes in the microbiome. In specific embodiments, administration of an effective amount of a composition will be for a time sufficient to effect treatment. In a particular embodiment, the method comprises administration and consumption of a composition comprising vitamin C and soy protein for a period of time sufficient to result in effective treatment and maintenance An effective amount may be based on several factors, including a dog's ideal weight, the age, gender, level of activity, the metabolizable energy of the composition, and the frequency of feeding the compositions, e.g., once, twice, or three times daily, and other compositions fed to the dog. In some embodiments an effective amount refers to an amount of soy protein and vitamin C administered based upon total nutritional intake, wherein the amount of soy protein is equal to 3.7-6.9% of total nutritional intake per day and the amount of vitamin C is equal to 104.8-148.2 ppm of total nutritional intake per day. In some embodiments an effective amount refers to a pet food comprising, on a dry matter basis for total nutritional intake per day, 3.7-6.9% soy protein and 104.8-148.2 ppm vitamin C. That is, the amount of food suitable to meet all daily nutrition and energy requirements for a canine subject contains, on a dry matter basis, 3.7-6.9% soy protein and 104.8-148.2 ppm vitamin C.

In some embodiments an effective amount refers to an amount of soy protein and vitamin C administered so based upon total nutritional intake, the amount of soy protein is equal to 4.8-5.8% of total nutritional intake per day and the amount of vitamin C is equal to 119.1-137.9 ppm of total nutritional intake per day. In some embodiments an effective amount refers to a pet food comprising, on a dry matter basis for total nutritional intake per day, 4.8-5.8% soy protein and 119.1-137.9 ppm vitamin C. That is, the amount of food suitable to meet all daily nutrition and energy requirements for a canine subject contains, on a dry matter basis, 4.8-5.8% soy protein and 119.1-137.9 ppm vitamin C.

In some embodiments an effective amount refers to an amount of soy protein and vitamin C administered so based upon total nutritional intake, the amount of soy protein is equal to 5.3% of total nutritional intake per day and the amount of vitamin C is equal to 126.5 ppm of total nutritional intake per day. In some embodiments an effective amount refers to a pet food comprising, on a dry matter basis for total nutritional intake per day, 5.3% soy protein and 126.5 ppm vitamin C. That is, the amount of food suitable to meet all daily nutrition and energy requirements for a canine subject contains, on a dry matter basis, 5.3% soy protein and 126.5 ppm vitamin C.

A "food," "food composition," or "pet food composition" can, in some embodiments, be a nutritionally complete diet for the animal, such as a dog, to which it is fed.

As used herein, an "ingredient" refers to any component of a composition.

The term "nutrient" refers to a substance that provides nourishment. In some cases, an ingredient may comprise more than one "nutrient," for example, a composition may comprise corn comprising important nutrients including both protein and carbohydrate.

Food compositions can be provided to an animal, such as but not limited to a pet, in the form of pet food. A variety of commonly known types of pet foods are available to pet owners. The selection of pet food includes but is not limited to wet pet food, semi-moist pet food, dry pet food and pet treats. Wet pet food generally has a moisture content greater than about 65%. Semi-moist pet food typically has a moisture content between about 20% and about 65% and may include humectants, potassium sorbate, and other ingredients to prevent microbial growth (bacteria and mold). Dry pet food such as but not limited to food kibbles generally has a moisture content below about 15%. Pet treats typically may be semi-moist, chewable treats; dry treats in any number of forms, chewable bones or baked, extruded or stamped treats; confection treats; or other kinds of treats as is known to one skilled in the art.

As used herein, the term "kibble" or "food kibble" refers to a particulate pellet like component of animal feeds, such as dog and cat feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced animal food compositions. A "nutritionally complete diet" is a diet that includes sufficient nutrients for maintenance of normal health of a healthy dog on the diet. Nutritionally complete and balanced pet food compositions, e.g., for canines, are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

It is contemplated that in feeding a dog a diet comprising an effective amount of vitamin C and soy protein, a preferred method comprises feeding the dog a food that contains vitamin C and soy protein. In other embodiments, feeding a dog a diet comprising an effective amount of vitamin C and soy protein is achieved by administering the dog vitamin C and soy protein as a supplement or treat. Whether delivered in a pet food composition or as a separate supplement or in a treat, providing the dog with the vitamin C and soy protein by any means is considered feeding a dog a diet comprising an effective amount of vitamin C and soy protein, As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like A diet may comprise vitamin C and soy protein in an effective amount to reduce elevated levels of 4-EPS in a canine. A diet that comprises vitamin C and soy protein is useful to treat anxiety in a canine. A diet that comprises vitamin C and soy protein is useful to treat stress in a canine. A diet that comprises vitamin C and soy protein is useful to promote of beneficial microbial growth and inhibit harmful microbial growth in the canine subject's microbiome, particularly the microbiome of the gastrointestinal track.

Compositions and Formulations

Application of the methodology outlined above has identified effective amounts of soy protein and vitamin C that provide significant benefits to dogs identified as being predisposed to elevated levels of 4-EPS and thus at an increased risk of developing anxiety, an increased risk of developing anxiety stress and an increased risk of inhibiting beneficial microbial growth and promoting harmful microbial growth in the canine's microbiome, in particular the gut microbiome. In some embodiments, the effective amounts of soy protein and vitamin C are components that have been combined with other ingredient to provide a nutritionally complete diet. In some embodiments, the food product is a nutritionally complete diet for an adult canine. In a specific aspect, the food product is a nutritionally complete diet formulated for an adult companion canine.

In some embodiments, the compositions include food compositions is suitable for consumption by a companion animal, particularly a dog, that comprise effective amounts of vitamin C and soy protein in combination with protein and/or fat and/or carbohydrate. In some embodiments, for example, in addition to vitamin C and soy protein, a nutritionally complete and balanced dog food composition may comprise: from 4% to 90%, from 4% to 75%, from 5% to 75%, from 10% to 60% protein, or from 15% to 50% by weight of protein based on the total weight of the composition on a dry matter basis; from 0% to 90%, from 2% to 80%, from 5% to 75%, and from 10% to 50% by weight of carbohydrate based on the total weight of the composition on a dry matter basis; and from 2% to 60%, from 5% to 50%, and from 10% to 35% by weight of fat based on the total weight of the composition on a dry matter basis. In some embodiments, for example, in addition to vitamin C and soy protein, a nutritionally complete and balanced dog food composition may further contain from 0 to 15% or from 2% to 8%, by weight of other vitamins, and minerals, antioxidants, and other nutrients, e.g. amino acids which support the nutritional needs of the animal. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

In addition to an effective amount of soy protein, in some embodiments, proteins useful as ingredients of the food compositions may comprise proteins from animal sources, such as animal proteins, including mammalian, avian protein, reptilian, amphibian, fish, invertebrate proteins and combinations thereof e.g., from any of cattle, sheep, pig, goat, deer, rabbit, horse, kangaroo, their milk, curds, whey or blood, and internal tissues and organs such as smooth muscle, striate muscle, liver, kidney, intestine or heart; chicken including internal tissues and organs such as smooth muscle, striate muscle, liver, kidney, intestine or heart and chicken eggs, additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids such as but not limited to lauric acid, myristic acid, palmitic acid, palmitoleic acid, margaric acid, margaroleic acid, stearic acid, oleic acid, linoleic acid, g-linolenic acid, a-linolenic acid, stearidonic acid, arachidic acid, gadoleic acid, DHGLA, arachidonic acid, eicossatetra acid, EPA, behenic acid, erucic acid, docosatetra acid, and DPA.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises one or more other vitamins, in addition to the effective amount of vitamin C, such as but not limited to vitamin A, vitamin D, vitamin E, *quinoa* grain, thiamine, riboflavin, niacin, pyridoxine, pantothenic acid, folic acid, vitamin B12, biotin, and choline.

In some embodiments, the food composition further comprises fiber, which may be supplied from a variety of sources, including, for example, vegetable fiber sources such as cellulose, beet pulp, peanut hulls, and soy fiber.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry matter basis of the composition).

Preparation of Compositions

The compositions that comprise vitamin C and soy protein may be prepared as food products suitable for consumption by dogs. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist" food products generally have a moisture content of from 25% to 35%. The food products may also include components of more than one consistency, for example, soft, chewy meat-like particles or pieces as well as kibble having an outer cereal component or coating and an inner "cream" component.

In some embodiments, the food products that comprise vitamin C and soy protein may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils water, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between species and breeds of animals, as well as one of more of the attributes of the animal. For example, canine foods, for example, are typically formulated based upon the life stage, age, size, weight, body composition, and breed.

In another embodiment, treats comprising an effective amount of soy protein and vitamin C can be prepared by, for example, an extrusion or baking process similar to those described below for dry food to provide an edible product. Treats include, for example, compositions that are given to an animal to entice the animal to eat during a non-meal time. Treats may be nutritional, wherein the composition comprises one or more nutrients, and may, for example, have a composition as described above for food. Non-nutritional treats encompass any other treats that are non-toxic. Compositions can be coated onto the treat, incorporated into the treat, or both.

In another embodiment, an animal toy is provided that is a chewable or consumable toy. Such toys are typically prepared by coating any existing toy with an effective amount of soy protein and vitamin C. Toys therefore include, for example, chewable toys. Contemplated toys for dogs include, for example, artificial bones. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones). It should be further recognized that this invention contemplates toys for companion animals and particularly for use by a cat or a dog.

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

The microbial metabolite, 4-ethylphenyl sulfate (4-EPS) is associated with stress and anxiety. Reduction in levels of 4-EPS has been shown to alleviate these symptoms.

A study was conducted using 30 adult dogs (between 4 and 10 years old) that showed an optimum combination of vitamin C and soy protein reduces circulating levels of the stress related microbial metabolite, 4-ethylphenyl sulfate (4-EPS).

Varying levels of soy protein (0 to 24 grams) were combined with varying levels of vitamin C (10.24 to 44.37 mg). This allowed each dog to have different intakes of vitamin C and soy protein, Blood is collected in order to determine plasma metabolomic profiles. Levels of 4-EPS in plasma can be measured by a commercial laboratory (Metabolon, Durham, N.C., USA). Extracted supernatant is split and run on gas chromatography and liquid chromatography mass spectrometer platforms. The peak for 4-EPS is known and the area under the peak for each sample can be normalized to a known sample. (See also: Evans, A. M., et al. (2009). Integrated, nontargeted ultrahigh performance liquid chromatography/ electrospray ionization tandem mass spectrometry platform for the identification and relative quantification of the small-molecule complement of biological systems. Anal. Chem. 81, 6656-6667.) Gas chromatography (for hydrophobic molecules) and liquid chromatography (for hydrophilic molecules) are used to identify and provide relative quantification of metabolites such as 4-EPS present in plasma samples. (See also: Ballet, C. et al. (2018) New enzymatic and mass spectrometric methodology for the selective investigation of gut microbiota-derived metabolites, Chem. Sci. 9, 6233-6239; Akiyama, Y et al. (2012) A Metabolomic Approach to Clarifying the Effect of AST-120 on 5/6 Nephrectomized Rats by Capillary Electrophoresis with Mass Spectrometry (CE-MS) Toxins 4(11):1309-1322; and Kikuchi K, et al. (2010) Metabolomic search for uremic toxins as indicators of the effect of an oral sorbent AST-120 by liquid chromatography/tandem mass spectrometry. J Chromatogr B Analyt Technol Biomed Life Sci 878:2997-3002.)

Circulating 4-EPS levels were determined and the correlation of intake of soy protein and vitamin C and the level of 4-EPS in blood was evaluated.

Dogs prone to having high 4-EPS may benefit from the consumption of food containing specific levels of vitamin C and soy protein. A matched-pair analysis comparing levels of 4-EPS in each dog after the consumption of the foods showed a significant reduction in 4-EPS due to the added vitamin C and soy protein (P=0.04).

Daily intakes of vitamin C and soy protein that lead to low levels of 4-EPS are indicated in Table 1. Varying combination of soy protein and vitamin C were evaluated for their potential to reduce the levels of circulating 4-EPS in adult dogs. As intake of vitamin C and soy protein increased, circulating levels of 4-EPS increased and then surprisingly decreased with increasing intake. The lowest level of 4-EPS was detected after a daily consumption of 10 grams of soy protein with 23.9 mg of vitamin C (Table 1). The average intake of the adult dogs was 188.9 grams. Therefore, the consumption of a food containing, as a dry matter basis, approximately 5.3% soy protein combined with 126.5 ppm vitamin C would result in the lowest level of 4-EPS. The highest level of 4-EPS, 1.22468, was detected after the consumption of 24 grams of soy protein with 44.4 mg of vitamin C. Pets had greater than average levels of 4-EPS after the consumption of low or no soy protein (0-3 grams) with 10.2-14.3 mg of vitamin C or high soy protein (18-24 grams) with 34.8-44.4 mg of vitamin C. Low levels of 4-EPS were achieved with a daily consumption of 7-13 g (3.7-6.9%) of soy protein and 19.8-28 mg (104.8-148.2 ppm) of vitamin C. The levels of 4-EPS were lower when consuming 9-11 grams (4.8-5.8%) of soy protein with 22.5-25.3 mg (119.1-137.9 ppm) vitamin C per day. The levels of 4-EPS were lowest when consuming 10 grams (5.3%) soy protein and 23.9 mg (126.5 ppm) vitamin C per day.

TABLE 1

Combination of soy protein and vitamin C to reduce circulating levels of 4-EPS

| Food Intake (g) | Soy protein (g) | Percent soy in food | Vitamin C (mg) | Vitamin C (PPM) | 4-EPS |
|---|---|---|---|---|---|
| 90 | 0 | 0 | 10.23948 | 54.205823 | 1.00328 |
| 102 | 1 | 0.5293806 | 11.604744 | 61.433266 | 0.963428 |
| 114 | 2 | 1.0587612 | 12.970008 | 68.660709 | 0.927584 |
| 126 | 3 | 1.5881419 | 14.335272 | 75.888152 | 0.895748 |
| 138 | 4 | 2.1175225 | 15.700536 | 83.115596 | 0.86792 |
| 150 | 5 | 2.6469031 | 17.0658 | 90.343039 | 0.8441 |
| 162 | 6 | 3.1762837 | 18.431064 | 97.570482 | 0.824288 |
| 174 | 7 | 3.7056644 | 19.796328 | 104.79792 | 0.808484 |
| 186 | 8 | 4.235045 | 21.161592 | 112.02537 | 0.796688 |
| 198 | 9 | 4.7644256 | 22.526856 | 119.25281 | 0.7889 |
| 210 | 10 | 5.2938062 | 23.89212 | 126.48025 | 0.78512 |
| 222 | 11 | 5.8231869 | 25.257384 | 133.7077 | 0.785348 |
| 234 | 12 | 6.3525675 | 26.622648 | 140.93514 | 0.789584 |
| 246 | 13 | 6.8819481 | 27.987912 | 148.16258 | 0.797828 |
| 258 | 14 | 7.4113287 | 29.353176 | 155.39003 | 0.81008 |
| 270 | 15 | 7.9407094 | 30.71844 | 162.61747 | 0.82634 |
| 282 | 16 | 8.47009 | 32.083704 | 169.84491 | 0.846608 |
| 294 | 17 | 8.9994706 | 33.448968 | 177.07236 | 0.870884 |
| 306 | 18 | 9.5288512 | 34.814232 | 184.2998 | 0.899168 |
| 318 | 19 | 10.058232 | 36.179496 | 191.52724 | 0.93146 |
| 330 | 20 | 10.587612 | 37.54476 | 198.75469 | 0.96776 |
| 342 | 21 | 11.116993 | 38.910024 | 205.98213 | 1.008068 |
| 354 | 22 | 11.646374 | 40.275288 | 213.20957 | 1.052384 |
| 366 | 23 | 12.175754 | 41.640552 | 220.43701 | 1.100708 |
| 390 | 24 | 12.705135 | 44.37108 | 234.8919 | 1.22468 |

When provided in effective amounts, soy protein and vitamin C reduce circulating levels of 4-EPS. Anti-stress food for pets can be formulated by inclusion of effective amounts of soy protein and vitamin C thereby reducing blood levels of the microbial toxin, 4-EPS, which when increased is associated with stress, anxiety and brain damage. Such pet foods thereby address stress-related problems associated with elevated circulating levels of 4-EPS in pets.

Example 2

The following composition is based upon total nutrition to be provided per day.

In some embodiments based on the total weight of the composition on a dry matter basis, the amount of soy protein is equal to 3.7-6.9% and the amount of vitamin C is equal to 104.8-148.2 ppm. In some embodiments, based on the total weight of the composition on a dry matter basis, the compositions comprise chicken in an amount from 5% to 25%, egg protein in an amount from 4% to 15%, corn gluten meal in an amount from 6% to 20%, vegetables thereof, in an amount from 0.5% to 2%, fruit in an amount from 0.5% to 2%, and a carbohydrate selected from millet, brewers rice, oat groats, and combinations thereof in an amount of 5% to 50% based on the total weight of the composition on a dry matter basis.

In some embodiments based on the total weight of the composition on a dry matter basis, the amount of soy protein is equal to 4.8-5.8% and the amount of vitamin C is equal to 119.1-137.9 ppm. In some embodiments based on the total weight of the composition on a dry matter basis, the amount of soy protein is equal to 5.3% and the amount of vitamin C is equal to 126.5 ppm.

In certain embodiments, compositions may comprise chicken in an amount of 5%, 7.5%, 10%, 12.5%, 15%, 17.5%, 20%, 22.5% or 25% based on the total weight of the composition on a dry matter basis. In certain embodiments, compositions may comprise egg protein in an amount of 4%, 5%, 6%, 7%, 8%, 9%, 10%, 11%, 12%, 13%, 14% or 15% based on the total weight of the composition on a dry matter basis. In certain embodiments, compositions may comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In certain embodiments, compositions may comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise a fruit source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

Example 3

Table 2 describes certain embodiments having proportion of the composition (% of dry matter weight of component composition).

TABLE 2

| | |
|---|---|
| Soy Protein | from about 3.7-6.9%, or from about 4.8-5.8%, or about 5.3% |
| Vitamin C | from about 104.8-148.2 ppm, or from about 119.1-137.9 ppm, or about 126.5 ppm. |
| Other Protein | from about 5% to about 70%, or from about 10% to about 70%, or from about 10% to about 60% |
| Carbohydrate (preferably a nitrogen-free or essentially nitrogen-free extract) | from about 0% to about 50%, or from about 5% to about 45% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins other than vitamin C, and minerals) | from about 0% to about 15%, or from about 2% to about 8% |

A daily diet that comprises vitamin C and soy protein may provide benefit to dogs identified as having stress. In some embodiments, the methods comprise identifying a dog as having or suspected of having stress, a stress disorder or displaying symptoms of stress or a stress disorder and feeding it a daily diet that comprises vitamin C and soy protein.

Example 4

Table 3 describes ingredients used in certain embodiments having proportion of the composition (% of dry matter weight of component composition).

TABLE 3

| Description | Content Range (w/w %) |
|---|---|
| Soy Protein | 3.7-6.9 |
| Vitamin C | 0.012-0.034 |
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |

Example 5

Table 4 describes ingredients used in certain embodiments having proportion of the composition (% of dry matter weight of component composition).

TABLE 4

| Ingredient | w/w % |
|---|---|
| Soy Protein | 5.3 |
| Vitamin C | 0.023 |
| Chicken, livers, hydrolyzed, dry | 32.79-36.79 |
| Corn, starch, common canning | 28.45-32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | 4.00 |
| Cellulose, coarse | 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | 2.50 |
| OatWell ® 22 oat bran | 3.00 |
| Pecan Fiber | 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |

Example 6

Table 5 describes ingredients used in certain embodiments having proportion of the composition (% of dry matter weight of component composition).

TABLE 5

| Ingredient | w/w % |
|---|---|
| Soy Protein | 3.7-6.9 |
| Vitamin C | 0.012-0.034 |
| Rice, brewers | 23.00-25.00 |
| Pea, protein concentrate | 9.00-10.00 |
| Chicken Dried 10% Ash | 7.00-9.00 |
| Chicken, ground, fresh | 6.00-7.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flav Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |

TABLE 5-continued

| Ingredient | w/w % |
|---|---|
| Mineral, premix, 2305 | 0.04 |
| Oat Fiber, Fruit, Vegetable blend | 0.04 |
| Dicalcium phosphate | 0.04 |

Example 7

Table 6 describes ingredients used in certain embodiments having proportion of the composition (% of dry matter weight of component composition).

TABLE 6

| Ingredient | w/w % |
|---|---|
| Soy Protein | 3.7-6.9 |
| Vitamin C | 0.012-0.034 |
| Rice, Brewers | — |
| Chicken Meal | 6.00-7.00 |
| Pea, protein concentrate | 7.00-8.00 |
| Cellulose, coarse | 3.00-4.00 |
| Chicken Dried 10% Ash | 5.00-6.00 |
| Barley, pearled, cracked | 18.00-20.00 |
| Chicken, ground, fresh | 7.00-8.00 |
| Flax, seed, whole | 2.00 |
| Coconut oil preserved | 4.00 |
| Chicken, liver, digest, optimizor LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |

Example 8

Table 7 describes ingredients used in certain embodiments having proportion of the composition (% of dry matter weight of component composition).

TABLE 7

| Ingredient | w/w % | w/w % |
|---|---|---|
| Soy Protein | 3.7-6.9 | 3.7-6.9 |
| Vitamin C | 0.012-0.034 | 0.012-0.034 |
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizor LDPE H | 2.00 | 2.00 |
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flav Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | 7.00 | — |
| Flax seed whole brown | 3.00 | — |
| Beet pulp, ground, fine | 2.50 | — |
| Cranberry pomace | 1.00 | — |

Example 9

Table 8 describes ingredients used in certain embodiments having proportion of the composition (% of dry matter weight of component composition).

TABLE 8

| Ingredient | w/w % | w/w % |
|---|---|---|
| Soy Protein | 3.7-6.9 | 3.7-6.9 |
| Vitamin C | 0.012-0.034 | 0.012-0.034 |
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | 26.00 | 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |

Example 10

Table 9 describes ingredients used in certain embodiments having proportion of the composition (% of dry matter weight of component composition).

TABLE 9

| Ingredient | w/w % | w/w % | w/w % | w/w % | w/w % |
|---|---|---|---|---|---|
| Soy Protein | 3.7-6.9 | 3.7-6.9 | 3.7-6.9 | 3.7-6.9 | 3.7-6.9 |
| Vitamin C | 0.012-0.034 | 0.012-0.034 | 0.012-0.034 | 0.012-0.034 | 0.012-0.034 |
| Coconut Oil | up to 14.2 | up to 7.1 | up to 14.2 | up to 13.0 | up to 13.0 |
| Protein | up to 19.7 | up to 24.7 | up to 24.7 | up to 24.8 | up to 24.8 |
| Fat | up to 20.6 | up to 16.9 | up to 16.9 | up to 22.0 | up to 22.0 |
| Carbohydrate | up to 53.8 | up to 51.0 | up to 51.0 | up to 46.3 | up to 27.6 |
| Crude Fiber | up to 0.37 | up to 2.6 | up to 2.6 | up to 1.4 | up to 21.0 |

The invention claimed is:

1. A method for treating anxiety or stress in an animal, the method comprising:
    administering to the animal in need thereof an effective amount of soy protein and vitamin C, wherein the effective amount of the soy protein is from about 3.7% to 6.9% of nutritional intake per day, and wherein the effective amount of vitamin C is from about 104.8 ppm to 148.2 ppm of nutritional intake per day; and
    reducing levels of 4-ethylphenyl sulfate in the animal, wherein reducing levels of 4-ethylphenyl sulfate in the animal indicates treating anxiety or stress in the animal.

2. The method of claim 1 wherein the animal is a canine.

3. The method of claim 1, further comprising identifying the canine as having an elevated level of 4-ethylphenyl sulfate, and/or as having canine anxiety, and/or as having canine stress symptoms.

4. The method of claim 1 wherein the animal is administered a food composition comprising the soy protein and the vitamin C.

5. The method of claim 4 wherein the animal is a canine.

6. The method of claim 5, further comprising identifying the canine as having an elevated level of 4-ethylphenyl sulfate, and/or as having canine anxiety, and/or as having canine stress symptoms.

7. The method of claim 1 wherein the animal is administered a food composition comprising the soy protein and the vitamin C, wherein the soy protein is equal to 4.8-5.8% of nutritional intake per day and vitamin C at a level of 119.1-137.9 ppm of nutritional intake per day.

8. The method of claim 7 wherein the animal is a canine.

9. The method of claim 8, further comprising identifying the canine as having an elevated level of 4-ethylphenyl sulfate, and/or as having canine anxiety, and/or has as having canine stress symptoms.

10. The method of claim 1, wherein the animal is administered a food composition comprising the soy protein and the vitamin C, wherein the soy protein is equal to 5.3% of nutritional intake per day and vitamin C at a level of 126.5 ppm of nutritional intake per day.

11. The method of claim 10 wherein the animal is a canine.

12. The method of claim 11, further comprising identifying the canine as having an elevated level of 4-ethylphenyl sulfate, and/or as having canine anxiety, and/or has as having canine stress symptoms.

13. The method of claim 3, wherein the method comprises identifying the canine as having an elevated level of 4-ethylphenyl sulfate, wherein identifying the canine as having an elevated level of 4-ethylphenylsulfate comprises evaluating a blood sample of the canine.

14. The method of claim 3, wherein the method comprises identifying the canine as having canine anxiety, wherein the canine anxiety is identified with symptoms of canine anxiety, wherein the symptoms comprise one or more of aggression, urinating or defecating in the house, drooling, panting, destructive behavior, depression, excessive barking, pacing, restlessness, repetitive or compulsive behavior, or combinations thereof.

15. The method of claim 3, wherein the method comprises identifying the canine as having an elevated level of 4-ethylphenyl sulfate, wherein the method further comprises reducing the elevated levels of 4-ethylphenyl sulfate with the effective amount of the soy protein and the vitamin C.

16. The method of claim 1, wherein the method comprises identifying the canine in need thereof as being predisposed to an elevated level of 4-ethylphenyl sulfate.

17. A method of treating a canine suffering from anxiety or stress, the method comprising:
    measuring an elevated level of 4-ethylphenyl sulfate in a canine in need thereof relative to a control value from a normal canine or population of canines, and/or relative to a previous individual value from the canine; and
    treating the canine by administering the canine an effective amount of soy protein and vitamin C, wherein the effective amount of the soy protein is from about 3.7% to 6.9% of nutritional intake per day, and wherein the effective amount of vitamin C is from about 104.8 ppm to 148.2 ppm of nutritional intake per day.

18. The method of claim 16, wherein the elevated level of 4-ethylpheyl sulfate in the canine in need thereof is measured from a blood sample of the canine in need thereof.

* * * * *